United States Patent [19]

DeMarinis et al.

[11] Patent Number: 4,465,677

[45] Date of Patent: Aug. 14, 1984

[54] PHARMACEUTICAL COMPOSITIONS AND METHOD OF PRODUCING ALPHA$_2$ ANTAGONISM

[75] Inventors: Robert M. DeMarinis, Ardmore; Jacob P. Hieble, Philadelphia; William D. Matthews, West Chester, all of Pa.

[73] Assignee: Smithkline Beckman Corporation, Philadelphia, Pa.

[21] Appl. No.: 398,015

[22] Filed: Jul. 14, 1982

[51] Int. Cl.$^3$ ............................................ A61K 31/55
[52] U.S. Cl. .............................. 424/244; 260/239 BB
[58] Field of Search ........................................ 424/244

[56] References Cited

U.S. PATENT DOCUMENTS

| | | | |
|---|---|---|---|
| 3,716,639 | 2/1973 | Hoegerle et al. | 260/239 BB |
| 3,752,892 | 8/1973 | Hoegerle et al. | 260/239 BB |
| 3,906,006 | 9/1975 | Brossi et al. | 260/465 D |
| 4,210,749 | 7/1980 | Shetty | 549/243 |
| 4,233,217 | 11/1980 | Shetty | 260/239 BB |
| 4,265,890 | 5/1981 | Holden et al. | 424/244 |

OTHER PUBLICATIONS

Hoeggerle et al., Chem. Abs. 125489a, vol. 74 and 90330w, vol. 72.

*Primary Examiner*—Jane T. Fan
*Attorney, Agent, or Firm*—Joseph A. Marlino; Stuart R. Suter; Alan D. Lourie

[57] ABSTRACT

Pharmaceutical compositions and method of producing alpha$_2$ antagonism by administering N-substituted 2,3,4,5-tetrahydro-1H-3-benzazepines.

11 Claims, No Drawings

PHARMACEUTICAL COMPOSITIONS AND METHOD OF PRODUCING ALPHA$_2$ ANTAGONISM

This invention relates to pharmaceutical compositions and a method of producing alpha$_2$ antagonism by employing certain N-substituted 2,3,4,5-tetrahydro-1H-3-benzazepines.

The pharmaceutical compositions and methods of this invention produce alpha$_2$ antagonism, a pharmacological action which is associated with a broad spectrum of cardiovascular activity. For example, the compounds of this invention may be used for treating congestive heart failure, angina pectoris, and thrombosis.

Advantageously, the compounds also produce a reduction in blood pressure and are therefore useful as antihypertensive agents. This invention also relates to a method of producing antihypertensive activity by administering these compounds.

DESCRIPTION OF PRIOR ART

U.S. Pat. Nos. 4,210,749 and 4,233,217 disclose a broad class of benzazepines being useful as analgesics, antihistaminics and narcotic antagonists. However, there is no specific disclosure of the compounds of Formula I. Moreover, there is no suggestion in these patents that the compounds of Formula I would be useful as alpha$_2$ antagonists or for reducing blood pressure. One specific compound of Formula I, 6-chloro-3-methyl-2,3,4,5-tetrahydro-1H-3-benzazepine has been disclosed as a chemical intermediate in U.S. Pat. No. 4,265,890. There is no suggestion in this patent that the compound has any useful biological activity. U.S. Pat. Nos. 3,716,639 and 3,752,892 disclose 7-chloro and 6-chloro-2,3,4,5-tetrahydro-1H-3-benzazepines as anorexigenic agents.

None of the above known art discloses the biological activities of the claimed compositions and methods.

DESCRIPTION OF INVENTION

The N-substituted 2,3,4,5-tetrahydro-1H-3-benzazepine compounds which are the active ingredients of the pharmaceutical compositions of this invention and are used in the methods of this invention are represented by the following formula:

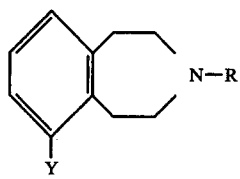

Formula I in which:

R is hydrogen or a straight chain lower alkyl of from 1 to 3 carbon atoms; and

X is halogen such as chloro or bromo, and a pharmaceutically acceptable acid addition salt thereof.

A particularly preferred compound in the pharmaceutical compositions and methods of this invention is a compound of Formula I in which R is methyl and X is chloro being the compound 6-chloro-2,3,4,5-tetrahydro-3-methyl-1H-3-benzazepine.

The above compounds of Formula I which are the active ingredients in the compositions and method for producing alpha$_2$ antagonism are prepared by synthetic methods familiar to the art. The most advantageous procedure is as follows:

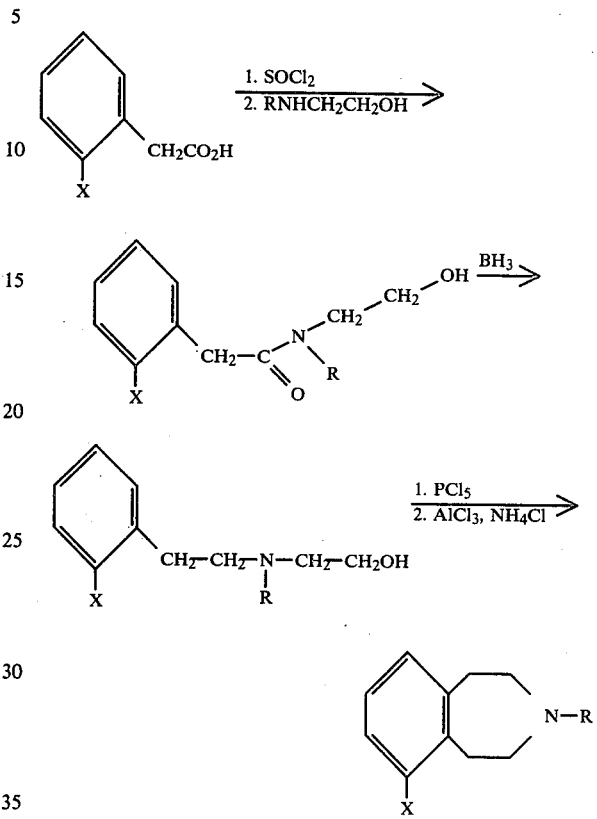

The terms X and R are as defined above.

According to the above procedure, a halophenyl acetic acid is treated with thionyl chloride followed by an appropriate amino alcohol. The resultant amide is reduced by any well known agent such as, for example, borane. The resultant amino alcohol is then converted to the corresponding halide and cyclized under Friedel-craft conditions.

The pharmaceutically acceptable acid addition salts having the utility of the free bases of Formula I, prepared by methods well known to the art, are formed with both inorganic or organic acids, for example: maleic, fumaric, benzoic, ascorbic, pamoic, succinic, bis-methylenesalicylic, methanesulfonic, ethanedisulfonic, acetic, oxalic, propionic, tartaric, salicylic, citric, gluconic, aspartic, stearic, palmitic, itaconic, glycolic, p-aminobenzoic, glutamic, benzenesulfonic, hydrochloric, hydrobromic, sulfuric, cyclohexylsulfamic, phosphoric and nitric acids.

The activity of the compounds of Formula I is demonstrated in vitro by determining the prejunctional alpha$_2$-antagonist activity using the isolated superfused guinea pig left atrium. Briefly, the heart is removed from a pentobarbital-anesthetized male guinea pig. The left atrium is removed, dissected free of extraneous tissue and mounted in a 2 ml. superfusion chamber. The tissue is placed at 60 pulse/minute and the sympathetic nerves excited at 6 minute intervals by field stimulation. The response to nerve stimulation is measured as the difference in contractile force between the basal contraction and peak contraction following a nerve stimulation. A concentration-response curve for clonidine (alpha$_2$-agonist) is prepared by administering an increasing concentration of clonidine following each successive stimulation. The tissue is then superfused with the alpha$_2$-antagonist to be tested for thirty minutes and the clonidine concentration-effect curve was repeated in the presence of antagonist. The receptor dissociation constant of the antagonist ($K_B$) is defined as the antagonist concentration required to shift the log concentration-response curve of the agonist to the right by a factor of 2.

Selectivity for the alpha$_2$ vis-a-vis the alpha$_1$-adrenoceptor is determined by comparing the $K_B$ obtained as described above with the $K_B$ on the alpha$_1$ receptor determined in the rabbit ear artery segment as an antagonist of the constrictor response induced by norepinephrine. (Hieble and Pendleton, *Arch. Pharmacol.*, 309, 217–224 (1979)).

A preferred compound of this invention is 6-chloro-2,3,4,5-tetrahydro-3-methyl-1H-3-benzazepine hydrochloride which has a $K_B$ value in the isolated perfused guinea pig left atrium of 13 nM.

The antihypertensive activity of the compounds of this invention is demonstrated in vivo as follows:

Male rats (300–450 g.) are anesthetized with sodium brevital and the femoral vein and artery are cannulated. Cannulas are run intradermally so as to be externalized in the dorso-sacral area of either side and kept in place by wound clips. The rats are allowed to regain consciousness after being placed in a small animal restrainer. The arterial cannula is connected to a pressure transducer for constant blood pressure and heart rate monitoring. Drugs are administered either orally via gavage, or i.v. via the femoral vein cannula at a rate of 0.06 ml./minute.

The above test is conducted on both normotensive and hypertensive rats. DOCA Salt hypertensive rats are prepared from male uninephrectomized Sprague-Dawley rats. The rats, approximately six weeks of age, are lightly anesthetized with ether and subcutaneously implanted with a 25-mg. deoxycorticosterone acetate pellet in the left dorso-sacral area. Six days later a second pellet is implanted in the right dorso-sacral area. These rats are fed a normal laboratory diet, but are given 1% saline solution to drink in place of water. The rats are kept on the saline drinking water for 22–24 days.

The following table sets forth the effect of 6-chloro-2,3,4,5-tetrahydro-3-methyl-1H-3-benzazepine on blood pressure after i.v. administration to both normotensive and hypertensive rats.

TABLE 1

| Type of Rats | Diastolic Blood Pressure | | |
|---|---|---|---|
| | Pre Drug | Post Drug 0.5 mg./Kg. | Decrease BP (MMHg) 1.0 mg./Kg. I.V. |
| Normotensive (control) (Sprague-Dawley) (n = 4) | 95 ± 7 MMHg | 6 ± 2 | 13 ± 1 |
| DOCA Salt Hypertensive (n = 4) | 135 ± 5 MMHg | 27 ± 3 | 33 ± 4 |
| Normotensive (control) (Wistar-Kyoto) (n = 4) | 115 ± 3 MMHg | 7 ± 2 | 10 ± 2 |
| Spontaneously Hypertensive (n = 7) | 167 ± 3 MMHg | 33 ± 7 | 46 ± 2 | n = Number of rats

The data in Table 1 demonstrate that while 6-chloro-2,3,4,5-tetrahydro-3-methyl-1H-3-benzazepine has little effect on diastolic blood pressure in normotensive rats, it produced a marked drop in diastolic blood pressure in both DOCA Salt and spontaneously hypertensive rats. Moreover, comparison of the 0.5 mg./kg. and 1.0 mg./kg. doses shows that the antihypertensive effect is dose-related.

The effect of the oral administration of 6-chloro-2,3,4,5-tetrahydro-3-methyl-1H-3-benzazepine on blood pressure in the DOCA-salt hypertensive rat was also determined. Table 2 below sets forth the results of this test.

TABLE 2

| Dose (PO) | Mean Arterial Pressure | | Δ BP (MM Hg) |
|---|---|---|---|
| | Pre-Drug | Post-Drug | |
| 2 mg/kg | 148 ± 11 | 131 ± 12 | 17 ± 3 |
| 5 mg/kg | 160 ± 7 | 127 ± 5 | 34 ± 4 |
| 10 mg/kg | 167 ± 8 | 99 ± 4 | 68 ± 8 |

The pharmaceutical compositions used to carry out the method of producing alpha$_2$ antagonism and antihypertensive activity comprise a pharmaceutical carrier and, as the active ingredient, a benzazepine compound of Formula I. The active ingredient will be present in the compositions in an effective amount to produce alpha$_2$ antagonism and antihypertensive activity.

Preferably, the compositions contain the active ingredient of Formula I in an amount of from about 25 mg. to about 500 mg., advantageously from about 50 mg. to about 250 mg., per dosage unit.

The pharmaceutical carrier may be for example a solid or a liquid. Exemplary of solid carriers are lactose, magnesium stearate, terra alba, sucrose, talc, stearic acid, gelatin, agar, pectin or acacia. The amount of solid carrier will vary widely but preferably will be from about 25 mg. to about 1 gm. Exemplary of liquid carriers are syrup, peanut oil, olive oil, sesame oil, propylene glycol, polyethylene glycol (mol. wt. 200–400) and water. The carrier or diluent may include a time delay material well known to the art such as, for example, glyceryl monostearate or glyceryl distearate alone or with a wax.

A wide variety of pharmaceutical forms can be employed, for example, the preparation may take the form of tablets, capsules, powders, troches, lozenges, syrups, emulsions, sterile injectable liquids or liquid suspensions or solutions.

The pharmaceutical compositions are prepared by conventional techniques involving procedures such as mixing, granulating and compressing or dissolving the ingredients as appropriate to the desired preparation.

The method of producing alpha$_2$ antagonism and antihypertensive activity according to this invention comprises administering to a subject in an amount sufficient to produce these activities a benzazepine compound of Formula I.

Preferably, the compounds of Formula I are administered in conventional dosage unit forms prepared by combining an appropriate dose of the compound with standard pharmaceutical carriers.

Preferably, the active ingredient of Formula I will be administered in a daily dosage regimen of from about 100 mg. to about 1000 mg., most preferably from about 200 mg. to about 500 mg. Advantageously, equal doses will be administered preferably two to four times per day. When the administration is carried out as described above, alpha$_2$ antagonism and antihypertenvise activity is produced.

The route of administration of the pharmaceutical compositions of this invention and in accordance with the methods of this invention is internal, either parenteral or preferably oral, in an amount to produce the desired biological activity.

The inventors have a co-pending application, Ser. No. 325,249, which discloses the use of the compounds of Formula I where R is lower alkyl as agents for reducing intraocular pressure.

The following examples are not limiting but are illustrative of the compounds of this invention and processes for their preparation. The temperatures are in degrees Centigrade.

EXAMPLE 1

A mixture of 125 g. (0.73 mol) of O-chlorophenylacetic acid, 155 g. (1.3 mol) of thionyl chloride and 2-3 drops of dimethylformamide in 1500 ml. of toluene was stirred at room temperature for three hours. The toluene was evaporated under reduced pressure to give an oil which was dissolved in 200 ml. of methylenechloride. This was added dropwise to a solution of 165 g. (2.2 mol) of N-methylamino ethanol in 1 liter of methylene chloride. After addition was complete, the solution was stirred at room temperature for three hours. The organic solution was washed with water, dilute hydrochloric acid and saturated sodium chloride, dried over magnesium sulfate, filtered and evaporated to give 2-chloro-N-(2-hydroxyethyl)-N-methylbenzeneacetamide as a crystalline solid, m.p. 77°.

To 400 ml. of a 1 mol solution of borane in tetrahydrofuran was added dropwise a solution of 43 g. of the above amide in 350 ml. of tetrahydrofuran at a rate sufficient to maintain a gentle reflux. After addition was complete, the solution was refluxed for two hours, cooled in an ice bath and treated carefully with dilute hydrochloric acid to destroy excess borane. The majority of the solvent was removed under vacuum and the residue heated on a steam bath for one hour. The mixture was diluted with 300 ml. of water and extracted with ether. The aqueous layer was made basic with 40% sodium hydroxide and extracted with ether. The combined basic extracts were washed with water and saturated sodium chloride, dried and evaporated to give 2-[[2-(2-chlorophenyl)-ethyl]methylamino]ethanol.

A suspension of 36 g. (0.173 mol) of phosphorous pentachloride in 300 ml. of methylene chloride was treated dropwise with a solution of 37 g. (0.173 mol) of the 2-[[2-(2-chlorophenyl)ethyl]methylamino]ethanol in 150 ml. of methylene chloride. After addition was complete, the mixture was refluxed overnight, evaporated to dryness and partitioned between dilute hydrochloric acid and ether. The aqueous layer was made basic with 10% sodium hydroxide and extracted well with ether. The ether extracts were washed with water and saturated sodium chloride, dried over magnesium sulfate and filtered. Addition of a saturated solution of ethereal hydrochloric acid gave a solid precipitate which was removed by filtration, washed with ether and dried to give 2-chloro-N-(2-chloroethyl)-N-methylbenzene ethanamine hydrochloride, m.p. 110°.

To a mixture of 41.5 g. (0.155 mol) of the above chloro ethanamine hydrochloride and 6.26 g. (0.117 mol) of ammonium chloride was added 41 g. of anhydrous aluminum chloride. The reaction became homogenous, melted and exothermed. It was placed in an oil bath which had been heated to 175° and stirred for thirty minutes. An additional 20 g. of aluminum chloride was added and the mixture heated for another thirty minutes. A final 41 g. portion of aluminum chloride was added and the reaction heated for twenty hours. It was cooled to 140° and poured into 3 l. of ice water containing 300 ml. of concentrated hydrochloric acid and stirred for fifteen minutes. Sixty grams of sodium potassium tartrate was added and stirred until solution was effected. It was made basic with 40% sodium hydroxide, extracted twice with ether and the combined extracts washed with water, and saturated sodium chloride, dried and reduced in volume by half. Addition of a solution of saturated ethereal hydrochloric acid gave a solid precipitate which was collected, washed with ether and dried to give a white solid. Crystallization from methanol-ethyl acetate gave 6-chloro-3-methyl-2,3,4,5-tetrahydro-1H-3-benzazepine hydrochloride, m.p. 268°-270°.

EXAMPLE 2

| Ingredient | Amounts |
| --- | --- |
| 6-Chloro-2,3,4,5-tetrahydro-3-methyl-1H—3-benzazepine hydrochloride | 150 mg. |
| Lactose | 350 mg. |

The ingredients are mixed and filled into a hard gelatin capsule.

One capsule is administered four times a day.

EXAMPLE 3

| Ingredients | Amounts |
| --- | --- |
| 6-Chloro-2,3,4,5-tetrahydro-3-methyl-1H—3-benzazepine hydrochloride | 200 mg. |
| Calcium sulfate dihydrate | 150 mg. |
| Sucrose | 25 mg. |
| Starch | 15 mg. |
| Talc | 5 mg. |
| Stearic Acid | 3 mg. |

The calcium sulfate dihydrate, sucrose and the benzazepine are thoroughly mixed and granulated with 10% gelation solution. The wet granules are screened, dried and then mixed with the starch, talc and stearic acid, screened and compressed into a tablet.

One tablet is administered three times a day.

EXAMPLE 4

| Ingredient | Amounts |
| --- | --- |
| 6-Chloro-2,3,4,5-tetrahydro-1H—3-benzazepine hydrochloride | 500 mg. |
| Lactose | 50 mg. |

The ingredients are mixed and filled into a hard gelatin capsule.

One capsule is administered two times a day.

What is claimed is:

1. A method of producing alpha₂ antagonist activity which comprises administering to a subject requiring said activity an amount sufficient to produce said activity of a benzazepine compound of the formula:

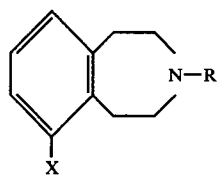

in which:

R is hydrogen or a straight chain lower alkyl of from 1 to 3 carbon atoms, and X is halogen such as chloro or bromo, or a pharmaceutically acceptable acid addition salt thereof.

2. The method of claim 1 in which R is methyl and X is chloro being the compound 6-chloro-2,3,4,5-tetrahydro-3-methyl-1H-3-benzazepine.

3. The method of claim 2 in the form of a hydrochloride salt.

4. The method of claim 1 which comprises administering a dosage unit containing from about 25 mg. to about 500 mg. of said benzazepine.

5. A pharmaceutical composition for producing alpha₂ antagonism comprising a pharmaceutically acceptable carrier and a benzazepine compound of the formula:

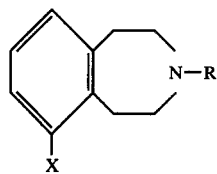

in which:

R is a straight chain lower alkyl of from 1 to 3 carbon atoms, and X is halogen such as chloro or bromo;

or a pharmaceutically acceptable acid addition salt thereof.

6. The pharmaceutical composition of claim 5 in which R is methyl and X is chloro being the compound 6-chloro-2,3,4,5-tetrahydro-3-methyl-1H-3-benzazepine.

7. The pharmaceutical composition of claim 6 in the form of a hydrochloride salt.

8. A method of producing antihypertensive activity which comprises administering to a hypertensive subject in an amount sufficient to produce said activity, a benzazepine compound of the formula:

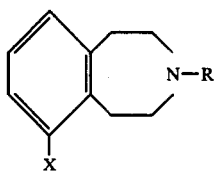

in which:

R is hydrogen or a straight chain lower alkyl of from 1 to 3 carbon atoms, and X is halogen such as chloro or bromo, or a pharmaceutically acceptable acid addition salt thereof.

9. The method of claim 8 in which the benzazepine compound is 6-chloro-2,3,4,5-tetrahydro-3-methyl-1H-3-benzazepine.

10. The method of claim 9 in the form of a hydrochloride salt.

11. The method of claim 8 which comprises administering a dosage unit containing from about 25 mg. to about 500 mg. of said benzazepine.

* * * * *